(12) United States Patent  
Ebi

(10) Patent No.: US 7,015,963 B2  
(45) Date of Patent: Mar. 21, 2006

(54) CCD SENSOR INCORPORATING PARALLEL DIFFUSION REGIONS WITHIN THE OUTPUT

(75) Inventor: Hiroyuki Ebi, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 684 days.

(21) Appl. No.: 10/183,050

(22) Filed: Jun. 27, 2002

(65) Prior Publication Data

US 2003/0001583 A1  Jan. 2, 2003

(30) Foreign Application Priority Data

Jun. 29, 2001 (JP) ............. P. 2001-198119

(51) Int. Cl.  
*H04N 5/335* (2006.01)

(52) U.S. Cl. ................ 348/294; 257/229

(58) Field of Classification Search ........... 348/294, 348/297, 311, 313, 315, 316, 375; 257/225, 257/229

See application file for complete search history.

(56) References Cited

U.S. PATENT DOCUMENTS 4,803,531 A    2/1989  Riley et al.
5,210,613 A *  5/1993  Lee ........................ 348/315
5,452,004 A *  9/1995  Roberts .................. 348/301
5,784,101 A *  7/1998  Hasegawa ............... 348/282
6,824,660 B1* 11/2004  Tomita ..................... 204/416

FOREIGN PATENT DOCUMENTS

EP    0 559 155 A1    9/1993
EP    0 881 486 A2   12/1998
EP    1 130 389 A1    9/2001

OTHER PUBLICATIONS

Japanese Abstract No. 2001033274, dated Feb. 9, 2001.

* cited by examiner

*Primary Examiner*—David L. Ometz  
*Assistant Examiner*—Adam L. Henderson  
(74) *Attorney, Agent, or Firm*—Sughrue Mion, PLLC

(57) ABSTRACT

In a CCD sensor in which electric charges derived from a plurality of detecting elements 2 are outputted from a signal output portion 9, two diffusion portions 22A and 22B are provided in a parallel manner to each other in the signal output portion 9, and electric charges outputted from a designated detecting element 2 are accumulated into one diffusion portions 22A so as to output the accumulated electric charges. Even in such a case that signal levels derived from detecting elements are low, such a CCD sensor capable of performing a high-precision measuring operation is provided, while a dynamic range of the CCD sensor is widened.

9 Claims, 5 Drawing Sheets

PPRIOR ART

CCD SENSOR INCORPORATING PARALLEL DIFFUSION REGIONS WITHIN THE OUTPUT

BACKGROUND OF THE INVENTION

The present invention is directed to a CCD sensor.

An apparatus capable of acquiring two-dimensional information by employing a CCD is known from, for instance, European Patent Publication EP-0881486 entitled "Method For Measuring Physical Phenomenon, or Chemical Phenomenon, and Equipment Thereof". As a sensor used in this measuring apparatus, such a CCD sensor is employed which is arranged by a plurality of physical/chemical sensors (unit sensors) sensible to physical/chemical phenomena, and also, a plurality of CCDs which transfer electric signal charges produced from these plural unit sensors.

FIG. 3 is a diagram for schematically indicating a structure of an upper surface of a CCD sensor which measures, for example, a two-dimensional distributing condition of pH. In this drawing, reference numeral 1 indicates a CCD sensor. This CCD sensor 1 is constituted by a plurality of unit elements (unit sensors) 2 sensible to hydrogen ions. While the upper surfaces of the respective unit elements 2 are covered by pH responsive films capable of sensing (responding) with respect to hydrogen ions corresponding to a measuring object, potentials are produced at boundary surfaces between the pH response film and a liquid in response to an amount of hydrogen-ion concentration, and a magnitude (namely, pH) of the hydrogen ion concentration is converted into an electric charge signal by utilizing a change of this potential. While, for example, 10 pieces of these unit sensors 2 are provided along a direction indicated by an arrow 4 so as to constitute a sensor column 3, for instance, 5 sets of these sensor columns 3 are arrayed along a direction indicated by an arrow 5 which is located perpendicular to the above-described arrow 4 so as to arrange the CCD sensor.

Reference numeral 6 shows a charge transfer portion for transferring electric charge signals produced in the respective unit sensors 2. This charge transfer portion 6 is arrayed by a plurality of vertical CCDs 7 and a single horizontal CCD 8, while the vertical CCDs 7 are arranged by a plurality of CCDs. Also, reference numeral 9 represents a signal output portion for outputting a signal derived from the horizontal CCD 8. Reference numeral 20 represents a diffusion portion of the signal output portion 9.

FIG. 4 illustratively shows a basic structure of the above-explained CCD sensor 1. In this drawing, reference numeral 10 indicates a semiconductor substrate made of, for instance, p type Si (silicon), the thickness of which is selected to be on the order of 500 micrometers.

A channel stopper 11, a charge supplying portion 12, a charge injection control portion 13, a sensor portion 14 functioning as a charge converting portion, a barrier portion 15, a CCD 6a which constitutes the charge transfer portion 6, a floating diffusion 16, a reset gate 17, a reset drain 18, and an output transistor 19 having an MOS structure are formed on the above-described semiconductor substrate 10.

Then, a single piece of unit sensor 2 is constituted by the respective members such as the charge supply portion 12, the charge injection control portion 13, the sensor portion 14, and the barrier portion 15. As will be later discussed more in detail, the sensor portion 14 constructs such a potential well which is constituted in such a manner that a depth of this potential well is changed in response to a magnitude of hydrogen-ion concentration. Also, the signal output portion 9 is constituted by the respective members such as the floating diffusion 16, the reset gate 17, the reset drain 18, and the output transistor 19.

Now, a principle idea of measuring operations of the above-described unit sensor 2 will be explained with reference to a potential diagram indicated in FIG. 5. When the measuring operation is carried out, a pulse voltage is applied to the charge supplying portion 12, the barrier portion 15, and the reset gate 17, whereas a DC voltage is applied to other electrodes except for the floating diffusion 16.

On the other hand, in an MOS structure using a p type semiconductor, the following fact is normally known. That is, since a positive voltage is applied to a metal electrode of the MOS structure, a depletion layer is formed on a boundary surface between an insulating film and the semiconductor in response to this positive voltage. As a consequence, while this phenomenon is used, potential states are produced in the vicinity of the boundary surface between the semiconductor and the insulating film, as represented in FIG. 5.

In a state as indicated in FIG. 5A, the potential of the charge supplying portion 12 is set to a high potential (namely, arrow direction is high potential), and electric charges 21 are not injected into the sensor portion 14.

In a state as indicated in FIG. 5B, since the potential of the charge supplying unit 12 is decreased, the electric charges 21 are injected into the sensor portion 14.

In a state as indicated in FIG. 5C, since the potential of the charge supplying unit 12 is increased, the electric charges 21 which have been cut off by the charge injection control portion 13 are stored into the sensor portion 14.

In a state as shown in FIG. 5D, since the potential of the barrier portion 15 is increased, the electric charges 21 which have been stored in the sensor portion 14 are transferred to the floating diffusion 16.

In a state as shown in FIG. 5E, after all of the electric charges 21 of the sensor portion 14 have been transferred to the floating diffusion 16, the barrier portion 15 is closed so as to stop the flow-in operation of the charges. At this stage, the potential of the floating diffusion 16 is determined based upon an amount of such transferred electric charges 21, this potential is inputted to the gate portion of the output transistor 19 having the MOS structure, and a drain current of this output transistor 19 is measured by a source follower circuit.

In a state as indicated in FIG. 5F, after the potential of the floating diffusion 16 has been read, the reset gate 17 is turned ON so as to reset the potential of the floating diffusion to the potential of the reset drain 18. Since this reset operation is performed, the potential state is again returned to the above-explained state shown in FIG. 5A. In other words, since the operations defined from the state of FIG. 5A to the state of FIG. 5F are repeatedly carried out, the electric charges can be derived outside the MOS structure.

In accordance with the CCD sensor having the above-described structure, phenomena occurred at a plurality of different positions can be measured at the same time. Since the magnitude of the hydrogen ion concentration is converted into the electric charges, either a one-dimensional distribution of pH or a two-dimensional distribution of pH can be easily acquired as an image by employing the charge transfer portion 6 constituted by a plurality of CCDs 6a. Furthermore, electric charges indicative of information as to plural points are stored, so that a very weak signal can be amplified. Accordingly, a very small change occurred in a phenomenon may also be firmly grasped.

As previously explained, in such a case that the two-dimensional information is obtained by employing the CCD, the electric charges appeared in the detecting elements 2 arranged in the two-dimensional manner are continuously carried to the diffusion portion 20 of the signal output portion 9, and then, are converted into the voltage by this diffusion portion 20. This voltage may be outputted outside this CCD. In such a case that a chemical amount such as ion concentration, or a physical amount such as a temperature, which are wanted to be measured, constitutes only a portion of an entire amount, and furthermore, a signal amount is small, S/N (signal-to-noise ratio) is necessarily determined based upon performance of an FET of the above-explained diffusion portion 20.

Under such a circumstance, the following idea may be conceived. That is, the areas of the respective detecting elements 2 may be increased so as to carry a large amount of electric charges. In this case, while potential inclinations (fringe effect) at the detecting elements 2 are not involved, there is a limitation in increasing of the above-described areas of these detecting elements 2. As a result, it is practically difficult to achieve sufficiently high S/N.

SUMMARY OF THE INVENTION

The present invention has been made to solve the above-described problem, and therefore, has an object to provide such a CCD sensor capable of performing a high-precision measuring operation even when signal levels derived from detecting elements are low, while maintaining a wide dynamic range.

To achieve the above-explained object, a CCD sensor, according to the present invention, is featured by that in a CCD sensor in which electric charges derived from a plurality of detecting elements are outputted from a signal output portion, two diffusion portions are provided in a parallel manner to each other in the signal output portion, and electric charges outputted from a designated detecting element are accumulated into one of these two diffusion portions so as to output the accumulated electric charges.

In the CCD sensor with employment of the above-explained structure, since the electric charges derived from the designated detecting element are accumulated so as to be produced, even when the signal levels acquired in this designated detecting element are low, the CCD sensor can perform the measuring operation in high precision and the dynamic range thereof can be made wide.

DETAILED DESCRIPTION OF THE PREFERRED EMBODIMNET

Figure 1:
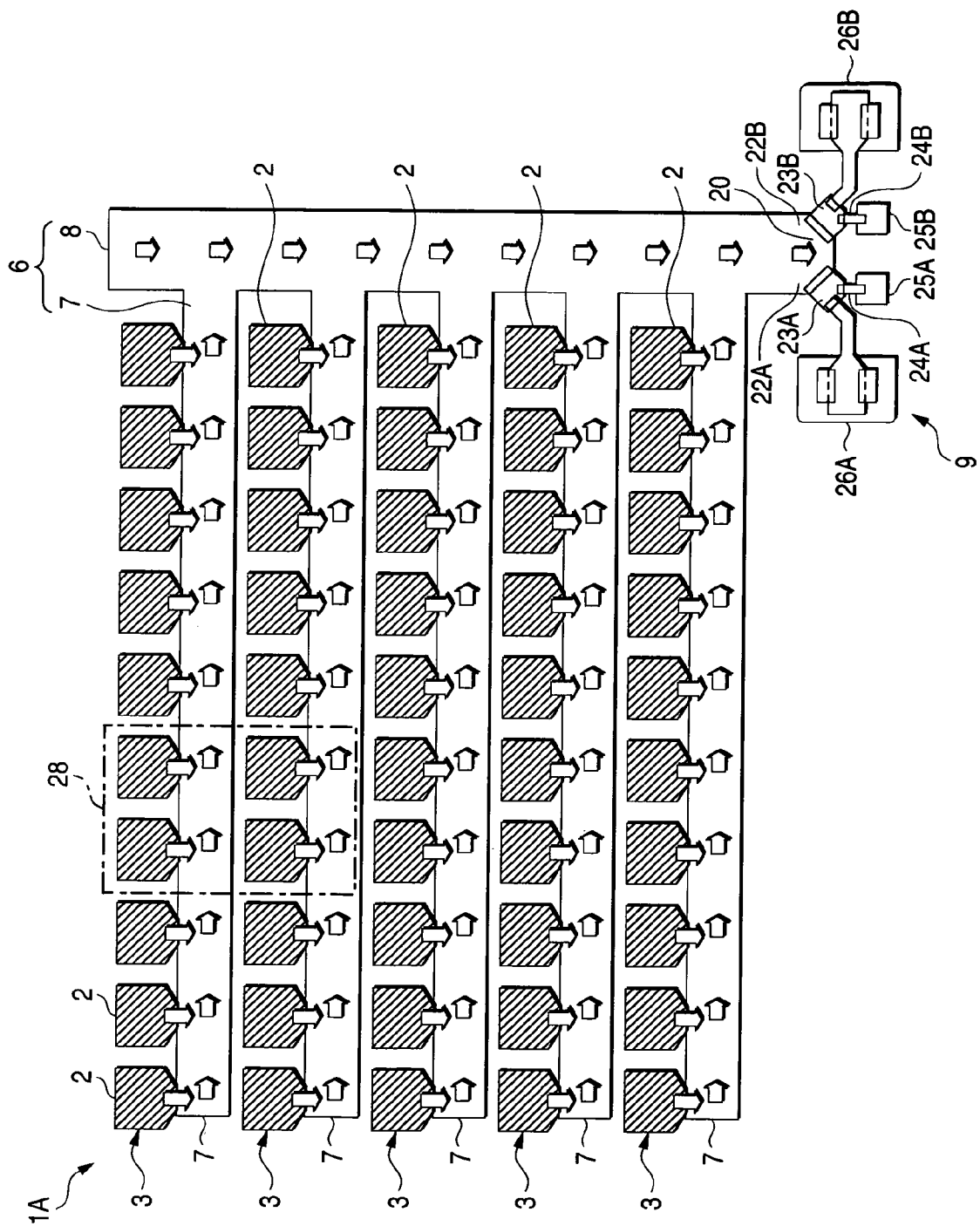
FIG. 1 is a diagram for schematically showing a structure of a CCD sensor according to the present invention.
Figure 2:
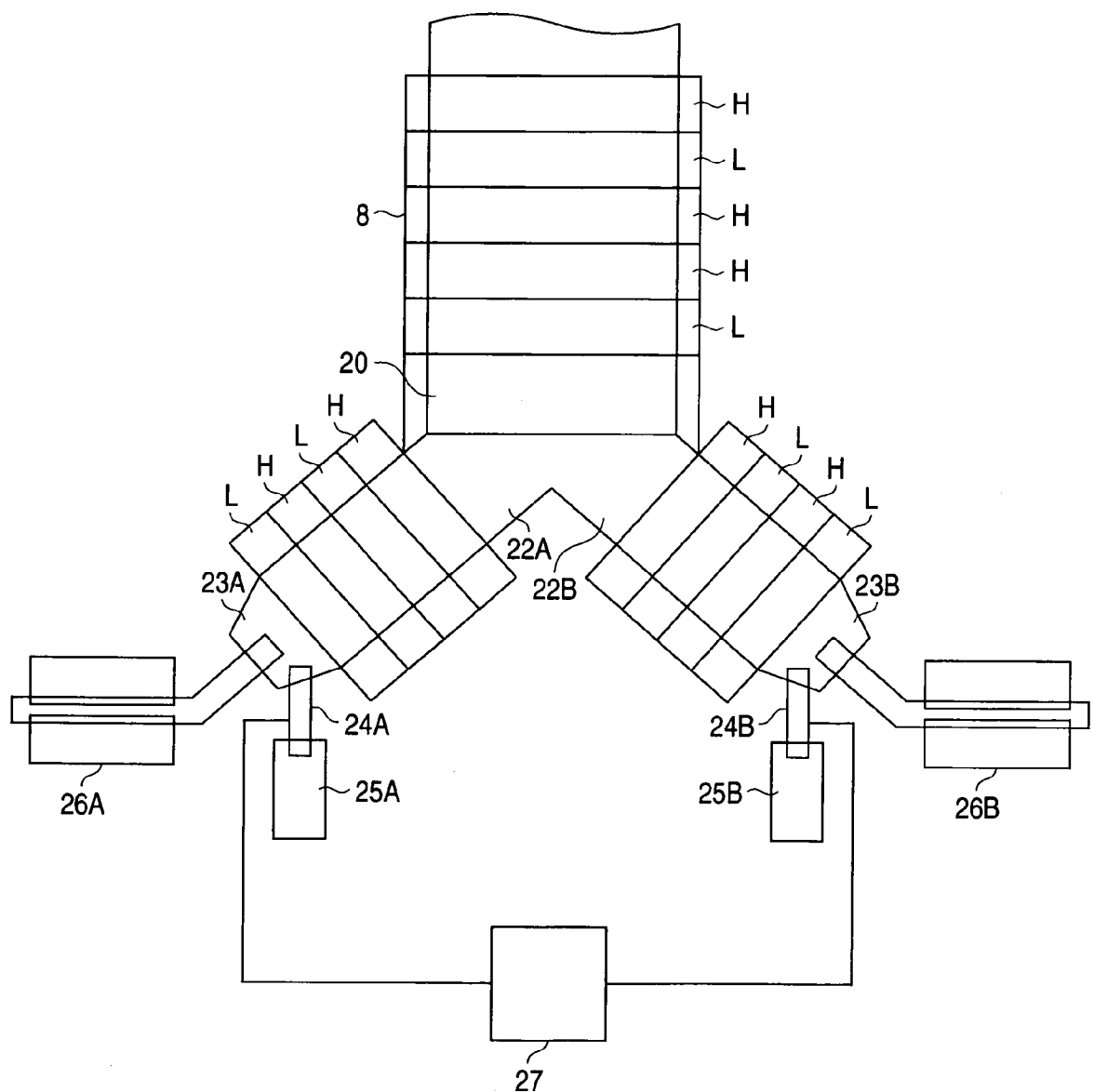
FIG. 2 is an enlarged diagram for showing a structure of a signal output portion of the above-described CCD sensor.
Figure 3:
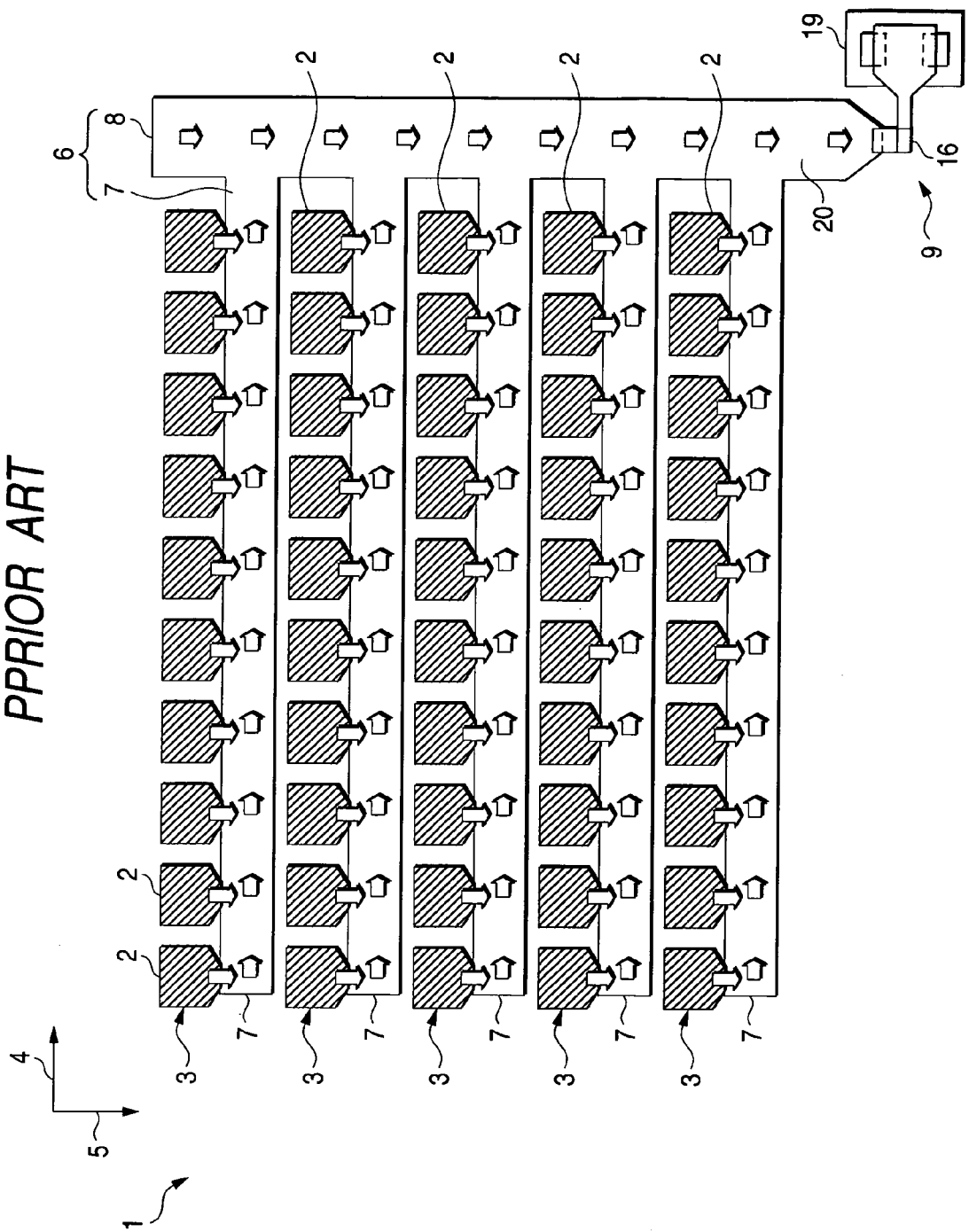
FIG. 3 is a diagram for schematically indicating the structure of the conventional CCD sensor.
Figure 4:
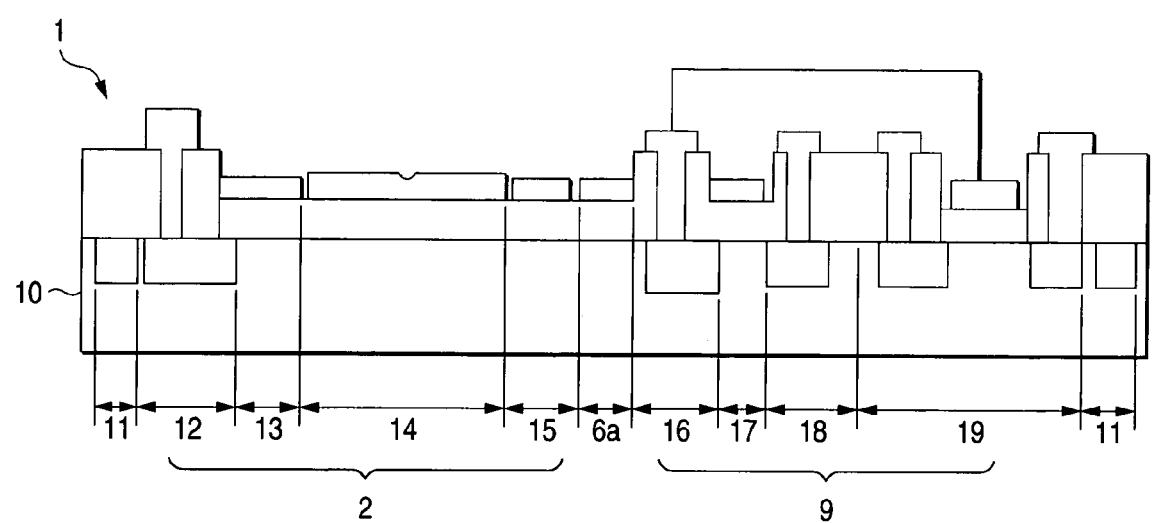
FIG. 4 is a diagram for schematically indicating the construction of the conventional CCD sensor.
Figure 5A:
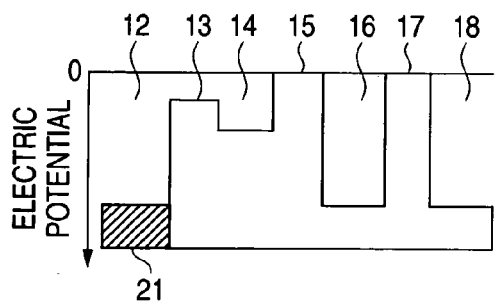
FIGS. 5A to 5F are explanatory diagrams for explaining the measuring principle idea of the conventional CCD sensor.
Figure 5D:
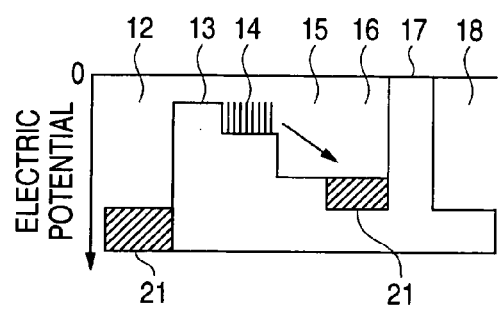
Figure 5B:
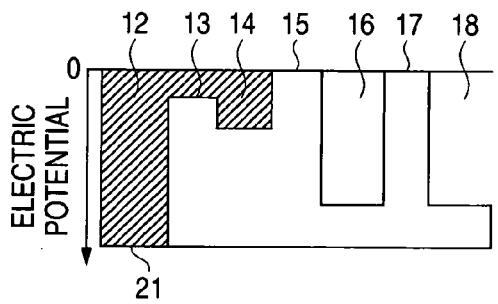
Figure 5E:
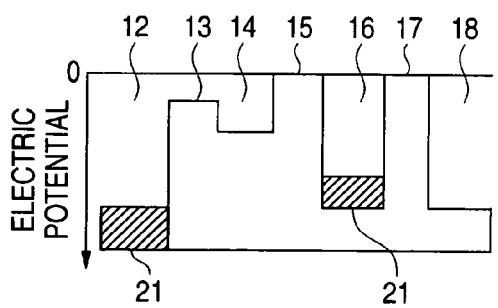
Figure 5C:
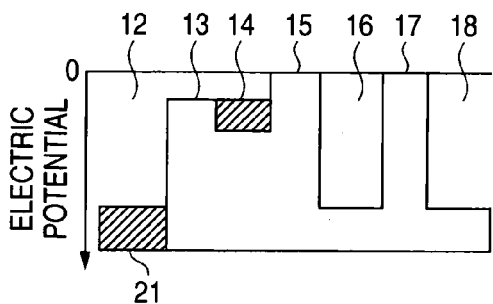
Figure 5F:
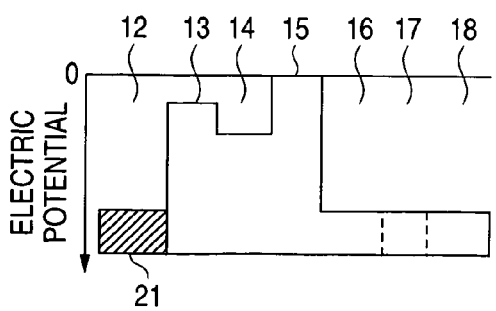

Referring now to drawings, the present invention will be described in detail. FIG. 1 and FIG. 2 indicate a CCD sensor 1A according to an embodiment mode of the present invention. This CCD sensor 1A of the present invention owns such a large different structure, as compared with that of the above-explained CCD sensor 1 shown in FIG. 3. That is, while two sets of diffusion portions 22A and 22B are provided in a parallel manner to each other in a signal output portion 9, outputs (electric charges) of a designated detecting element 2 are accumulated into one diffusion portion 22A to output the accumulated electric charges.

In other words, as shown in FIG. 1 and FIG. 2, reference numerals 22A and 22B indicate diffusion portions which are coupled to a diffusion portion 20 provided on the side of an output of a horizontal CCD 8, these diffusion portions 22A and 22B are arranged in a parallel manner to each other. One diffusion portion 22A constitutes a charge-accumulation diffusion portion, and the other diffusion portion 22B constitutes a normal charge-outputting diffusion portion. On an edge portion of each of these diffusion portions 22A and 22B, both a floating diffusion 23A and another floating diffusion 23B are formed, while reset gates 24A/24B, reset drains 25A/25B, and output transistors 26A/26B are electrically connected to these floating diffusions 23A/23B. Then, reference numeral 27 denotes a control portion for controlling the reset gates 24A and 24B. It should be noted that symbols "H" and "L" in FIG. 2 represent two phase electrodes used when the CCD sensor 1A is driven in a two phase mode.

Next, operations of the CCD sensor 1 having the above-described structure will now be explained. For instance, in FIG. 1, it is so assumed that signals derived from 4 detecting elements 2 located in such a region indicated by a dot and dash line 28 are accumulated. Electric charges which are derived from all of these detecting elements 2 including the detecting elements 2 in the above-described region 28 are entered via both the vertical CCD 7 and the horizontal CCD 8 into the diffusion portion 20 of the signal output portion 9. Then, the respective electric charges entered into the diffusion portion 20 may be allocated to the charge-accumulation diffusion portion 22A and the normal charge-outputting diffusion portion 22B by switching magnitudes (heights) of voltages at the electrodes "H" and "L" in this diffusion portion 20. In this case, only the electric charges outputted from the four detecting elements 2 located in the previously designated region 28 are inputted into the charge-accumulation diffusion portion 22A, whereas electric charges outputted from all of the detecting elements 2 which contain the four detecting elements 2 within the designated region 28 are inputted into the normal charge-outputting diffusion portion 22B except when they are transferred to the charge-accumulation diffusion portion 22A for accumulation.

Then, the electric charges derived from all of the detecting elements 2, which are entered into the normal charge-outputting diffusion portion 22B, are outputted therefrom every time the reset gate 24B is operated so as to produce an image signal in a similar manner to the operations of the conventional CCD sensor 1.

On the other hand, the charge electrics derived from the four detecting elements 2 located in the region 28, which are inputted into the charge-accumulation diffusion portion 22A, are stored only preset times, while the floating diffusion 23A connected to this charge-accumulation diffusion portion 22A is not reset every time. Thereafter, these electric charges are outputted from this charge-accumulation diffusion portion 22A so as to produce an image signal. As a result, even when the electric charges derived from the four detecting elements 2 located in this region 28 are small, these small electric charges are integrated with each other only preset times, so that the integrated electric charges may become a large signal and the resulting S/N may be improved. As a consequence, such a specific region which is wanted to be observed can be clearly observed.

Then, while a total integration time of the electric charges within the set region 28 may be properly set, and/or the area of this region 28 may be properly increased/decreased, such a measuring operation with a wide dynamic range may be carried out without lowering the transfer efficiency in the CCD sensor 1A.

In the above-described embodiment mode, the two-dimensional distribution of pH is observed by the CCD sensor 1A. However, the present invention is not limited to the above-described embodiment mode, but may be accomplished by that since the structure of the detecting elements 2 is properly changed, various sorts of chemical phenomena as well as various kinds of physical phenomena may be observed.

As previously described, in accordance with the present invention, in the CCD sensor in which the electric charges derived from a plurality of detecting elements are outputted from the signal output portion, two diffusion portions are provided in a parallel manner to each other in the signal output portion, and the electric charges outputted from the designated detecting element are accumulated into one of these two diffusion portions so as to output the accumulated electric charges. As a consequence, even when the signal levels acquired by these designated detecting elements are low, the CCD sensor can perform the measuring operation in high precision, while the dynamic range thereof can be widened. As a result, the specific region can be displayed as the high-precision image.

What is claimed is:

1. A CCD sensor in which electric charges derived from a plurality of detecting elements are outputted from a signal output portion, wherein:
    two diffusion portions are disposed parallel to each other in said signal output portion; and
    electric charges outputted from a designated detecting element are accumulated into one of said two diffusion portions, and electric charges outputted from all of said detecting elements are input into the other of said two diffusion portions.

2. A CCD sensor comprising:
    a plurality of detecting elements being arranged as a matrix;
    a charge transfer portion for transferring electric charge signals produced in said detecting elements; and
    a signal output portion for outputting a signal derived from the charge transfer portion,
    wherein said signal output portion has two diffusion portions disposed parallel to each other, and
    electric charges outputted from designated detecting elements are accumulated into one of said two diffusion portions, and electric charges outputted from all of said detecting elements are input into the other of said two diffusion portions.

3. The CCD sensor as claimed in claim 2, wherein each of said detecting elements comprises a charge supply portion, a charge injection control portion, a sensor portion, and a barrier portion.

4. The CCD sensor as claimed in claim 2, wherein said charge transfer portion comprises a plurality of charge coupled devices.

5. The CCD sensor as claimed in claim 2, wherein each diffusion portion comprises a floating diffusion disposed at edge portion being electrically connected to a reset gate, a reset drain and an output transistor.

6. The CCD sensor as claimed in claim 5, further comprising a control portion that controls said reset gate connected to each of said diffusion portions.

7. The CCD sensor as claimed in claim 2, wherein said designated detecting elements comprise a group of adjacent detecting elements within said matrix of detecting elements.

8. The CCD sensor as claimed in claim 7, wherein said group of detecting elements is disposed on an edge portion of said matrix of detecting elements.

9. The CCD sensor as claimed in claim 2, wherein said signal output portion and said diffusion portions comprise two phase electrodes that are used when said CCD sensor is driven in a two phase mode.

* * * * *